United States Patent
Labyed et al.

(10) Patent No.: US 11,166,699 B2
(45) Date of Patent: Nov. 9, 2021

(54) DIFFRACTION CORRECTION FOR ATTENUATION ESTIMATION IN MEDICAL DIAGNOSTIC ULTRASOUND

(71) Applicant: Siemens Medical Solutions USA, Inc., Malvern, PA (US)

(72) Inventors: Yassin Labyed, Maple Valley, WA (US); Kutay F. Ustuner, Mountain View, CA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 614 days.

(21) Appl. No.: 15/472,024

(22) Filed: Mar. 28, 2017

(65) Prior Publication Data
US 2018/0284251 A1   Oct. 4, 2018

(51) Int. Cl.
| | |
|---|---|
| A61B 8/00 | (2006.01) |
| A61B 8/08 | (2006.01) |
| G01S 15/89 | (2006.01) |
| G01S 7/52 | (2006.01) |

(52) U.S. Cl.
CPC ........ *A61B 8/5215* (2013.01); *G01S 7/52022* (2013.01); *G01S 7/52036* (2013.01); *G01S 7/52042* (2013.01); *G01S 7/52071* (2013.01); *G01S 15/8915* (2013.01); *G01S 15/8927* (2013.01); *G01S 15/8952* (2013.01); *A61B 8/4483* (2013.01); *A61B 8/461* (2013.01); *G01S 7/52095* (2013.01)

(58) Field of Classification Search
CPC .................................................. A61B 8/5269
See application file for complete search history.

(56) References Cited

U.S. PATENT DOCUMENTS

| | | | |
|---|---|---|---|
| 4,389,893 A | 6/1983 | Ophir et al. | |
| 4,993,416 A | 2/1991 | Ophir | |
| 7,353,709 B2 | 4/2008 | Kruger et al. | |
| 9,244,169 B2 | 1/2016 | Fan et al. | |
| 2004/0236222 A1* | 11/2004 | Mao | A61B 8/481 600/458 |
| 2005/0203405 A1* | 9/2005 | Tsujita | A61B 8/08 600/455 |

(Continued)

FOREIGN PATENT DOCUMENTS

| | | |
|---|---|---|
| CN | 102028499 A | 4/2011 |
| CN | 103619412 A | 3/2014 |

(Continued)

OTHER PUBLICATIONS

Fink, M., F. Hottier, and J. F. Cardoso. "Ultrasonic signal processing for in vivo attenuation measurement: Short time Fourier analysis." Ultrasonic imaging 5.2 (1983): Abstract.

(Continued)

*Primary Examiner* — Rajeev P Siripurapu

(57) ABSTRACT

For estimating attenuation, diffraction effects are corrected by transmitting at different frequencies using apertures sized to match the on-axis intensity profile and/or resolution cell size between the transmissions where there is no attenuation. Attenuation causes a variance in return. A rate of change is estimated from a ratio of the magnitude of the signals or displacements responsive to the transmissions. The attenuation is calculated from the rate of change over depth of the ratio.

18 Claims, 12 Drawing Sheets

(56) References Cited

U.S. PATENT DOCUMENTS

2007/0006651 A1 1/2007 Kruger et al.
2013/0345565 A1 12/2013 Fan et al.

FOREIGN PATENT DOCUMENTS

| GN | 103505243 A | | 1/2014 |
|---|---|---|---|
| JP | 2012170512 A | | 9/2012 |
| JP | 5747377 B2 | * | 7/2015 |

OTHER PUBLICATIONS

Insana, Michael F., et al. "Describing small-scale structure in random media using pulse-echo ultrasound." The Journal of the Acoustical Society of America 87.1 (1990): 179-192.

Kim, Hyungsuk, and Tomy Varghese. "Hybrid spectral domain method for attenuation slope estimation." Ultrasound in medicine & biology 34.11 (2008): 1808-1819.

Labyed, Yassin, and Timothy A. Bigelow. "A theoretical comparison of attenuation measurement techniques from backscattered ultrasound echoes." The Journal of the Acoustical Society of America 129.4 (2011): 2316-2324.

Narayana, Ponnada A., and Jonathan Ophir. "On the frequency dependence of attenuation in normal and fatty liver." IEEE Trans Son Ultrason 30.6 (1983): 379-383.

Ophir, J., et al. "Attenuation estimation in reflection: progress and prospects." Ultrasonic Imaging 6.4 (1984): Abstract.

Sasso, Magali, et al. "Controlled attenuation parameter (CAP): a novel VCTE™ guided ultrasonic attenuation measurement for the evaluation of hepatic steatosis: preliminary study and validation in a cohort of patients with chronic liver disease from various causes." Ultrasound in medicine & biology 36.11 (2010): 1825-1835.

Yao, Lin Xin, James A. Zagzebski, and Ernest L. Madsen. "Backscatter coefficient measurements using a reference phantom to extract depth-dependent instrumentation factors." Ultrasonic imaging 12.1 (1990): 58-70.

* cited by examiner

DIFFRACTION CORRECTION FOR ATTENUATION ESTIMATION IN MEDICAL DIAGNOSTIC ULTRASOUND

BACKGROUND

The present embodiments relate to medical diagnostic ultrasound.

Important pathological information may be obtained by characterizing the attenuation of ultrasound in tissue. The level of attenuation may be a biomarker for fatty liver disease. Cancers, such as breast cancer, may be diagnosed, in part, based on attenuation of ultrasound.

Attenuation may be measured using spectral analysis of radio frequency backscatter signals. A change in amplitude of power spectra as a function of depth of the acoustic backscatter indicates the attenuation. These backscatter approaches may suffer from variability, even with spectral averaging.

Accurate estimation of ultrasound attenuation requires effective elimination of diffraction effects. Diffraction effects have been reduced using a phantom. The phantom allows for calibration, reducing or removing the contribution of the imaging system, including diffraction. A ratio of signals from a patient to signals from the phantom acts to cancel the system contribution. The use of the phantom introduces errors due to the mismatch between the sound speed of the reference material (phantom) and the imaged tissue.

SUMMARY

By way of introduction, the preferred embodiments described below include a method, system, computer readable medium, and instructions for characterizing tissue in ultrasound imaging. The transmit diffraction effects are compensated for by transmitting pulses at two or more distinct center frequencies using apertures sized to match the on-axis transmit intensity profile between the transmissions for the no attenuation case. Attenuation changes the on-axis intensity profile between the transmissions. A rate of change is estimated from a ratio of the magnitude of the signals or displacements responsive to the transmissions. The attenuation is calculated from the rate of change over depth of the ratio.

In a first aspect, a method is provided for characterizing tissue with a medical diagnostic ultrasound scanner. First acoustic energy is transmitted at a first center frequency with a first aperture of a transducer array. Second acoustic energy is transmitted at a second center frequency with a second aperture of the transducer array, the second center frequency being different than the first center frequency, and the second aperture being different than the first aperture. A receive beamformer connected with the transducer array receives first and second signals responsive to the first and second acoustic energy, respectively. The first and second signals are responsive to tissue of a patient over depth. An image processor calculates a ratio of magnitudes of the first signals to the second signals as a function of the depth, fits a rate of change to the ratio as the function of the depth, and estimates attenuation of the tissue from the rate of change. An image of the attenuation for the patient is generated.

In a second aspect, a system is provided for estimating attenuation with ultrasound imaging. A transmit beamformer is configured to generate pulses at different frequency bands using different apertures, respectively. The sizes of the apertures are a function of the frequency bands. A receive beamformer is configured to output samples responsive to the pulses. An image processor is configured to estimate attenuation from the samples. A display is configured to display the attenuation.

In a third aspect, a method is provided for estimation of attenuation in tissue with a medical diagnostic ultrasound scanner. First acoustic energy is transmitted at a first center frequency with a first aperture of a transducer array. Second acoustic energy is transmitted at a second center frequency with a second aperture of the transducer array. The second center frequency is different than the first center frequency by a factor, and the second aperture is different than the first aperture by the inverse of the square root of the factor. A receive beamformer connected with the transducer array receives first and second signals responsive echoes of the first and second acoustic energy, respectively, from tissue. An image processor estimates the attenuation in the tissue from a ratio responsive to the first and second signals. An image of the attenuation for the patient is generated.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Ultrasound attenuation is estimated without using a phantom. Errors due to mismatch of a phantom with actual tissue of a patient are avoided in the estimated attenuation.

To correct for diffraction effects, transmissions are performed at multiple frequencies. The aperture size for each transmission is adjusted to match the on-axis intensity profile and/or resolution cell size for where there is no attenuation. Actual attenuation causes a mis-match, allowing for estimation of the attenuation.

In one approach, the ultrasound attenuation coefficient is estimated by transmitting two or more pulses with distinct center frequencies and substantially non-overlapping spectra. The effective aperture size of the transmit and receive beamformers is adjusted or set for each transmit pulse as a function of the respective center frequency. In preferred embodiment, the receive diffraction effects are also compensated for by adjusting the receive apertures to match the receive lateral resolution between transmissions. This can be achieved at all depths since the receive beamformer is typically a dynamic beamformer that has the capability to vary the focal depth and aperture size with time. The effective center frequency of the receive filter is adjusted to match the respective transmit pulse center frequency. The absolute bandwidth of the receive filter is kept the same between transmissions in order to also match the axial resolution. Calculating a ratio of the magnitude of the receive signals in respective frequency bands removes the diffraction effect. The attenuation coefficient is estimated by computing the rate of change of the ratio as a function of depth.

In another approach, acoustic force radiation impulse (ARFI) transmissions at different frequencies and apertures are used. Rather than using the magnitude of the receive signals from the transmission, the displacements responsive to the transmissions are tracked. The ratio of the displacements as a function of depth are used to estimate the attenuation.

Figure 1:
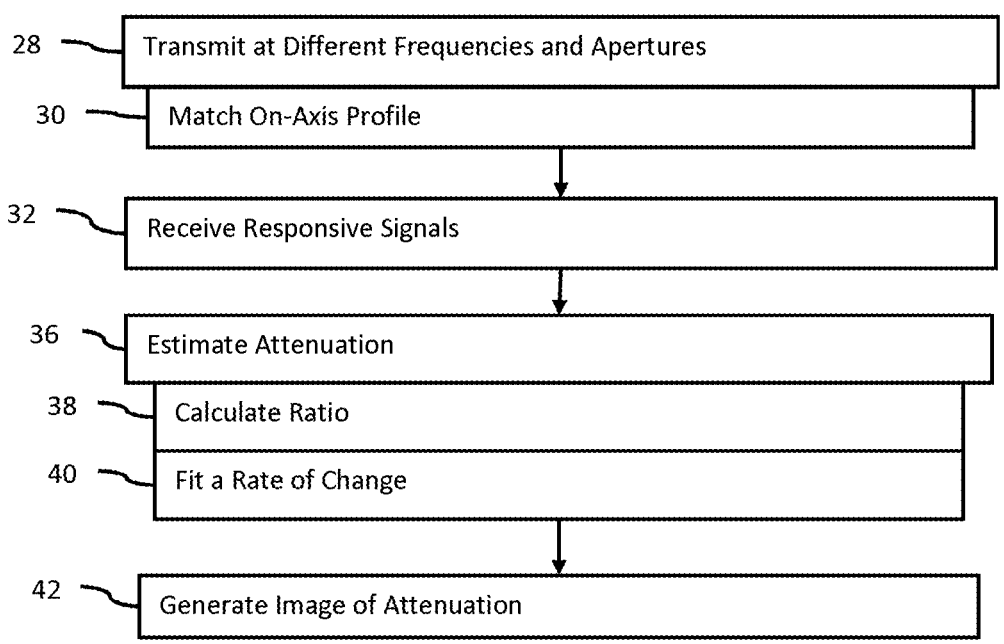
FIG. 1 is a flow chart of one embodiment of a method for estimating attenuation with a medical diagnostic ultrasound scanner.

FIG. 1 shows one embodiment of a flow chart diagram of a method for characterizing tissue with a medical diagnostic ultrasound scanner. The attenuation of ultrasound in tissue is estimated. Transmissions at different center frequencies have apertures sized based on the respective center frequencies to match the on-axis intensity profiles of the transmissions given no attenuation. A ratio of responsive information reflects distortion in the matching caused by the attenuation and is used to estimate the attenuation. A rate of change in the ratio is a function of the attenuation.

Figure 14:
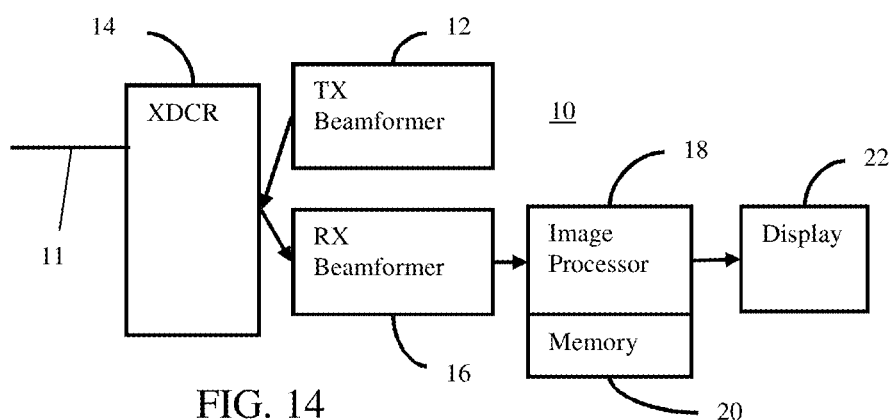
FIG. 14 is a block diagram of one embodiment of a system for ultrasound imaging.

The method is performed by the ultrasound imaging system 10 or scanner of FIG. 14, beamformers and an image processor, or a different system and/or processor. For example, the ultrasound scanner includes a transmit beamformer for transmitting acoustic energy from a transducer, a receive beamformer for receiving responsive signals using the transducer, and an image processor for estimating attenuation. A display generates an image of the attenuation.

The acts of FIG. 1 are performed in the order shown (top to bottom) or a different order. Additional, different, or fewer acts than shown in FIG. 1 may be used. For example, act 42 is not performed. As another example, acts for configuring the ultrasound scanner or B-mode imaging are added. In yet another example, act 30 is not performed as a separate act, but is part of act 28.

In act 28, the ultrasound scanner uses the transducer to transmit acoustic energy. For example, acoustic energy is focused at a location or region of interest by relative delay and/or phasing of channels of the transmit beamformer and corresponding elements of the transducer. The transducer is a one-dimensional (1D), 1.25D, 1.5D, 2D, planar, curved array or an annular array. Other arrays may be used. The transmit beamformer generates electrical waveforms for a transmit aperture. The elements of the transducer array within the aperture convert the electrical waveform into acoustic energy for acoustic transmission.

Within the tissue of the patient, the acoustic energy constructively interferes along one or more scan lines. A transmit beam is transmitted along a scan line. The transmit beam has a profile relative to the scan line. A center of the transmit beam includes a region of greater intensity. This region includes the focal location of the transmit beam. The transmit beam has a beam profile marked by locations of greater acoustic intensity. The acoustic intensity decreases with further lateral and/or depth (i.e., axial) spacing from the focal region. The region or beam profile may be defined based on an amount of reduction from a peak intensity, such as 3 dB, 6 dB, 10 dB, 20 dB or another amount of roll-off. Within the beam profile, greater acoustic intensity is provided.

The electrical waveforms and corresponding acoustic energy have any number of cycles. For a more broadband transmission, one, two or a few number (e.g., four or fewer) cycles are used. For a more narrowband transmission, five or more cycles are used, such as 6-8 cycles. Any envelope, type of pulse (e.g., unipolar, bipolar, or sinusoidal), or waveform may be used.

For attenuation estimation, transmit acoustic beams are formed at different transmit center frequencies and/or different frequency bands. The frequency bands do not overlap, but may overlap. The transmissions have different spectra. For example, the center frequency of one transmission is twice the center frequency of another transmission. Other factors than a factor of two may be used, such as a fractional factor (e.g., 0.66 or 1.75) or a larger integral (e.g., 3) factor.

The transmit beamformer transmits the acoustic energy with different center frequencies sequentially. The transmit beams are transmitted in separate transmit events. A transmit event is a contiguous interval where transmissions occur without reception of echoes responsive to the transmission. During the phase of transmitting, there is no receiving. Where a sequence of transmit events is performed, a corresponding sequence of receive events may also be performed. A receive beamformer of the ultrasound scanner generates samples in response to each transmit event. A receive event is performed in response to each transmit event and before the next transmit event. In this process, the transmit events or transmit and receive events at the different frequencies are performed as distinct events.

In other embodiments, the transmit beamformer transmits the acoustic energy with different frequencies, at least in part, simultaneously. The electric waveforms for two or more transmit beams along a same scan line but at different frequencies are combined or overlap in time as applied to the transducer. For at least some elements or channels, electric waveforms for multiple transmit beams sum together. One or more channels and elements may have waveform or acoustic energy from only one of the transmit beams, but others include, for at least part of the transmit event, waveform or acoustic energy from two or more of the transmit beams at a same time. As another approach, a transmit beam is formed with two distinct or different transmit frequencies, creating transmit beams at the different frequencies. The transmitted acoustic energy at different frequencies is transmitted in a single transmit event.

The acoustic energy is transmitted from an aperture. The transducer array includes selectable elements. The transmit beamformer selects the elements to include in an aperture. Any size aperture may be used. The aperture is fixed for transmit, but may vary during dynamic receive operation. The elements of a given aperture are contiguous, but sparse or other apertures may be used.

The apertures for the acoustic energy at the different frequencies are different. Each of the transmit beams at a different center frequency has a different aperture. The aperture is set as a function of the center frequency or frequency band. The aperture is set to match the on-axis beam profiles of the different transmit beams in act 30. Given the frequency of the transmitted acoustic energies, the respective apertures cause the on-axis beam profiles of the acoustic energy to be similar or match for where there is no attenuation. The on-axis pressure may be written as a function of depth z, aperture a, wavelength $\lambda = c/f$, the speed of sound in tissue c, and the transmit center frequency f, $P(z, \alpha, \lambda) = F(z')$, where z' is the further normalized distance given by $$z' = \frac{z}{a^2/\lambda}.$$

Therefore, the axial beam intensity profile is preserved by maintaining $\alpha^2/\lambda$ as a constant. For example, where the transmit frequency for one transmission is twice (factor of 2) the transmit frequency for the other transmission, then the apertures of the two transmissions have a size related by the square root of 2. The aperture for the transmitted acoustic energy with twice the center frequency is smaller than the aperture for the lower center frequency by the square root of 2. Reducing the frequency by a factor of 2 provides for increasing the aperture for that reduced frequency transmission by the square root of that factor (2). Conversely, the transmission with the greater frequency has a reduced aperture by the square root of the factor. The same relationship is used for any value of the factor.

The discussion above is for matching the on-axis transmit intensity profile. The match may not be exact. The match may provide for similar profiles. Similar is used to account for real world implementation differences from the mathematical ideal. The apertures may not be exactly related by the square root of the factor. Since the elements of the transducer are discrete, the apertures may be related by substantially the square root of the factor. The relationship may be for an effective aperture factoring in the acoustic apodization of the array due to frequency dependent element directivity. At one of the aperture settings, the relationship is substantially the square root of the factor. At other aperture settings during the dynamic operation, the relationship may be different but still within a few elements (e.g., 3 or fewer) of the square root of the factor. For the factor of 2, the relationship of the apertures is about 1/1.41=0.71, where about accounts for the effective (variation due to focus process) and/or substantial (variation due to use of discrete elements) alteration.

The transmitted acoustic energy is for scanning the patient. The transmit event is used to generate echoes that are received in a receive event. In an alternative embodiment, the transmission of the acoustic energy is to cause tissue displacement. Push pulses for Acoustic Radiation Force Impulse (ARFI) imaging are fired at two different frequencies and respectively scaled apertures. The pushing pulses have greater energy, such as by having many cycles (e.g., 100 or more cycles) and/or greater amplitude, so cause axial displacement of the tissue. The receive events are in response to other transmit events for tracking the tissue displacement.

The tissue axial displacement at position z from an ARFI push pulse at frequency $f_0$ is given by:

$$S_0(z, f_0) = \frac{cP(f_0)\beta_a(f_0)I(f_0, z)e^{-2\beta(f_0)z}}{E} \quad (1)$$

where c is a constant, $P(f0)$ is the transfer function of the transmitted pulse and the electro-mechanical response, $\beta_a(f0)$ is the frequency-dependent attenuation coefficient from absorption, $\beta(f0)$ is the frequency-dependent attenuation coefficient from both absorption and scattering ($\beta(f0) = \beta_a(f0) + \beta_s(f0)$, where $\beta_s(f0)$ is the attenuation coefficient from scattering), $I(f_0, z)$ is the acoustic intensity (on-axis diffraction pattern), and E is tissue elasticity.

The tissue displacement $S_0(z)$ at axial position z is estimated from the displacement profile at z. By transmitting and receiving at different times, the tissue at the different times is represented. By performing correlation or other similarity matching centered on the location of the scan line at depth z, the offset or displacement between times is found. A profile of displacement over time is measured from the ultrasound scanning. The maximum of the profile or the displacement at a time instant after the push may be used as the displacement for that location. Using the displacement at a given time from the push may avoid measuring for the profile or over many times. Instead, the tissue is scanned during a reference time (no or little displacement) and at the time instant after the ARFI.

The on-axis intensity is replicated by transmitting at frequency $f$ and setting the effective aperture size accordingly (inverse of square root of the factor relating the frequencies of the transmissions). The new axial displacement is given by:

$$S(z, f) = \frac{cP(f)\beta_a(f)I(f0, z)e^{-2\beta(f)z}}{E} \quad (2)$$

This displacement includes the relationship between frequency and aperture size used for the transmit and receive operations, so the displacements may be used to determine the attenuation just as the receive signals may be used. The transmit and receive events for measuring displacement may have any frequency and/or aperture.

In act 32, the ultrasound scanner receives signals responsive to the transmitted acoustic energy. The receive beamformer receives electric waveforms from transducer elements, which convert impinging echo signals from the acoustic energy into the electric waveforms. The waveforms are received in a receive event responsive to the transmit event. Waveforms responsive to the interaction of the transmitted acoustic energy with the tissue of the patient are received.

The reception is interleaved with the transmission of the sequence. For each transmit event, a receive event occurs. The receive event is a continuous interval for receiving echoes from the depth or depths of interest. The receive event occurs after ceasing the transmit event. After the transducer completes generation of acoustic energy for a given transmission, the transducer is used for reception of the responsive echoes. The transducer is then used to repeat another transmit and receive event pair for the same spatial location or locations, providing interleaving (e.g., transmit, receive, transmit, receive, . . . ) to measure the tissue response at the different frequencies with matching on-axis profiles.

The receive beamformer coherently sums the waveforms from the elements into beamformed signals. The reception is dynamic, providing signals over depth along a scan line. The beamformed signals are focused along the scan line, sampling tissue response along the scan line. The output of the receive beamformer are receive signals (e.g., samples) in a radio frequency or in-phase and quadrature format.

The receive beamformer uses an aperture for receiving the echoes. The aperture is substantially the same as used for transmit. For the transmit event with the frequency and aperture, the same or substantially same aperture is used for receive. For the transmit event with a different frequency and different aperture, substantially the same "different" aperture is used for receive. Substantially accounts for variation due to use of discrete elements and/or aperture variation due to dynamic focusing. In alternative embodiments, a different aperture is used for the receive event than for the transmit event to which the receive event is responsive.

The receive beamformer may include a filter, such as a band pass filter or a down-converter and a low pass filter. The filter reduces information at undesired frequencies. For example, harmonic or sub-harmonic information is reduced. The information at the desired frequency band is maintained or reduced less, such as maintaining information at the frequency band or center frequency of the corresponding transmit event. For example, the center frequency for one transmit event is 4 MHz. The filter maintains the information in the received signals at 4 MHz while reducing information at 2 MHz. Another transmission is at 2 MHz, so the filter maintains the information in the received signals at 2 MHz while reducing information at 4 MHz.

The aperture control on transmit is used to compensate for the diffraction. In a preferred embodiment, the receive diffraction effects are also compensated for by dynamic receive focusing using receive apertures sized to match the receive resolution cell size between the transmissions. This is achieved at all depths where the receive beamformer, unlike the transmit beamformer, is a dynamic beamformer that has the capability to vary the focal depth and aperture size with time. The effective center frequency of the receive filter is adjusted to match the respective transmit pulse center frequency. The absolute bandwidth of the receive filter is kept the same between transmissions in order to also match the axial resolution. For the case of a transmit center frequency ratio of $f_1/f_2=2$, matching the receive resolution cell size in the lateral dimension requires the ratio of the aperture at frequency $f_1$ to aperture at frequency $f_2$ to be ½. Since the round-trip resolution cell size is typically determined by the receive resolution cell size due to smaller f-numbers used on receive, the effects of diffraction on the resolution cell size may be compensated for by the receive compensation between transmissions as described above. The effects of diffraction on the on-axis intensity profile on the other hand is compensated for the transmit compensation described earlier.

For simultaneous transmission at different frequencies, the filter or separate filters create receive signals for the different frequencies. The focusing delays or phase may be a function of the frequency. The receive signals may be separately filtered to find the response to the different transmit frequencies. For sequential transmission, the different filters are used for sequential reception or the filter is reprogrammed to receive at the different frequencies at the different times. The filtering may be substantially at the same frequency as the respective transmit event. Substantially accounts for variation in the frequency as a function of depth to account for depth-based frequency shift.

Where ARFI transmission is used in act 28, the reception of act 32 is not of echoes to the ARFI transmission. Instead, the reception of act 32 is of receive signals responsive to tracking transmissions to measure displacement. The displacements caused by the sequential transmissions of ARFI at the different frequencies with respective different apertures are separately tracked, in part, by receiving signals responsive to tracking transmissions.

The displacements of tissue are measured at different depths. For the measurements at different depths, receive signals are acquired for the different depths.

In act 36, an image processor estimates the tissue attenuation. Based on the information responsive to the different transmit frequencies and respective apertures, the attenuation may be estimated without use of a phantom. The attenuation is estimated from a ratio, which is a function of the received signals from the different transmit frequencies and respective apertures. The rate of change of the ratio as a function of depth is used to calculate the attenuation. Acts 38 and 40 represent this use of the ratio and rate of change.

In act 38, the ratio is calculated. The ratio is of the magnitudes of the received signal envelope as a function of depth. Other magnitude or power calculations may be used. For each depth, the magnitude is calculated for each of the different transmissions. For two transmissions at different frequencies with respective different apertures, there are two magnitudes for each depth. The magnitudes for each depth are responsive to the transmissions at different frequencies. The ratio may be calculated as an average ratio of a reference to two or more other measures of magnitude.

Where the transmissions are narrow band, then the magnitude of the received signals are used for the ratio. Where the transmissions are broad band, then a Fourier transformation may be used. The received signals are Fourier transformed. The information at the desired center frequencies or band is selected. The ratio may be calculated in the frequency domain from the selected information. Alternatively, an inverse transformation is performed on the selected information and then the ratio of the magnitude of the selected information is calculated.

The ratio is calculated for each depth. The result is ratio as a function of depth. The ratio represents a difference in tissue response to the different frequencies and respective apertures over depth.

The power spectrum R obtained by averaging spectra from a number of windowed radio frequency signals at depth z and frequency f may be modeled as:

$$R(f,z)=D_t(f,z)D_r(f,z)B(f)P(f)T(f)e^{-4\alpha z f} \quad (3)$$

where, $D_t$ is the diffraction pattern on transmit, $D_r$ is the diffraction pattern on receive, B is the frequency-dependent backscatter coefficient, P is the transmit pulse frequency response, T is the round-trip transducer frequency response, and a is the attenuation coefficient. Combining depth-independent terms together into a G(f) term, the above equation becomes $$R(f,z) = D_t(f,z) D_r(f,z) G(f) e^{-4\alpha z f} \qquad (4)$$

For the case where we transmit at two distinct center frequencies $f_1$ and $f_2$ and compensate for the frequency dependence of the transmit and receive diffraction functions at all depths through transmit and receive aperture management as a function of the $$\frac{f_1}{f_2} \text{ ratio,}$$

and take the ratio of the two power spectra, providing:

$$\frac{R(f_1, z)}{R(f_2, z)} = G\left(\frac{f_1}{f_2}\right) e^{-4\alpha z \frac{f_1}{f_2}} \qquad (5)$$

In the preferred embodiment, the transmit aperture for the transmission with center frequency $f_2$ is set equal to the $\sqrt{f_1/f_2}$ times the transmit aperture at center frequency $f_1$. This equalizes the on-axis transmit intensity profile as a function of depth, which is the dominant transmit diffraction component. The dynamic receive aperture for the transmission with center frequency $f_2$ is set equal to the $f_1/f_2$ times the receive aperture at center frequency $f_1$ at all depths. This, along with equalizing the absolute bandwidth of the receive filter, equalizes the receive resolution cell size. This is the dominant component of the diffraction limited round-trip resolution cell size.

Both the exponential and the frequency dependent term G are unknown while the ratio is measured. By examining the exponential over depth for this ratio, the exponential is isolated for analysis.

Where ARFI is used, the ratio is of the displacements as a function of depth. For each depth, the ratio of the displacements responsive to ARFI at the different frequencies and respective apertures is calculated. Computing the ratio of the displacement gives:

$$R(z, f) = \qquad (6)$$
$$\frac{S(z, f)}{S_0(z, f0)} = \frac{P(f)}{P(f0)} \frac{\beta_a(f)}{\beta_a(f0)} e^{-2(\beta(f)-\beta(f0))z} = \frac{P(f)}{P(f0)} \frac{\beta_a(f)}{\beta_a(f0)} e^{-2\alpha(f-f_0)z}$$

where α is attenuation coefficient slope from both absorption and scattering, assuming the attenuation coefficient $\beta(f)$ is linear over a limited frequency band, i.e. $\beta(f) = \alpha f$. As noted for a ratio of magnitude of received signals, the ratio of displacements provides for one exponential term over depth. This allows solving for attenuation without solving for the other frequency dependent terms.

In act 40, the image processor fits a rate of change to the ratio as a function of depth. The ratio is logarithmic. The ratio begins at higher values and decreases to lower values with an increase in depth. Using least-squares, an exponential curve is fit to the ratio. The fit curve provides a rate of change. Alternatively, a natural logarithm of the ratio as a function of depth is calculated. The slope of the resulting line is the rate of change. In other embodiments, the exponential curve is treated as a line over a short depth extent.

The attenuation is estimated from the slope of that line. Windowing may be used to determine the fit at different depths.

The fit solves for the exponential term of equation 5 with respect to z. Since the frequency is known, the image processor estimates the attenuation of the tissue. The fit solves for the attenuation term. The correct attenuation provides for the line or exponential curve that fits the ratio as a function of depth. For the line, the slope is equal to $-2\alpha f_0$, from which the attenuation coefficient slope a can be estimated.

For a ratio from displacements, the attenuation coefficient is linear over a limited frequency band: $\beta(f) = \alpha f$, where a is the attenuation coefficient slope, which is estimated by fitting an exponential function to equation 6.

The attenuation is determined for a region of interest of tissue. For example, a point in a B-mode image is selected. The attenuation at that point is determined from a range of depths centered at the point. The attenuation may be determined for other points by similar windowing. For depths along a scan line, attenuation may be estimated for multiple locations along that scan line from the same transmit and receive events. For locations on other scan lines, other transmit and receive events may be used. A one, two, or three-dimensional distribution of attenuation may be estimated.

In act 42, the image processor and/or display device generates an image of the attenuation for the patient. The image processor, a display, a communications interface, or other device transmits the attenuation. The transmission is from and/or within the ultrasound scanner. The transmission is to another device, such as a memory, display, network, server, workstation, patient record database, and/or picture archiving and communications server. The attenuation is transmitted as data or imbedded in an image.

In one embodiment, the transmission is to a display. A value that is a function of the attenuation or other tissue characteristic is displayed as or as part of the image. The value is displayed as alphanumeric text. The value is the characteristic itself (e.g., value for attenuation) and/or is derived from the characteristic. In alternative or additional embodiments, the value is included as part of a graph, such as displaying the attenuation as a function of location.

The value is displayed alone or with another image. For example, a B-mode image or other image is provided with the value or values representing the tissue characteristic. Where the tissue characteristic is measured for one or more locations, alphanumeric text showing the value or values is provided as an annotation or overlay on the B-mode image.

In another embodiment, the value is part of an image spatially representing the tissue characteristic. For example, the attenuation is measured at two or more different locations. The values of the tissue characteristic for the different locations modulate the color, brightness, and/or shade of the image. Different pixels in the image show the corresponding tissue characteristic values through this modulation.

In one embodiment, shear wave imaging is performed. The shear wave speed is indicated at a user or processor selected location. Using the same ARFI used to generate the shear wave or a different ARFI, the attenuation or other tissue characteristic is calculated for that same location and presented. The scans used to calculate displacements for shear wave speed may also be used to calculate displacements on-axis, such as using parallel receive beamforming. Without additional sequencing or transmissions and receptions, both the shear wave speed and attenuation or other tissue characteristic are provided to the user for diagnosis.

The values are provided in a same image, adjacently displayed images, or sequentially displayed images.

Figure 2:
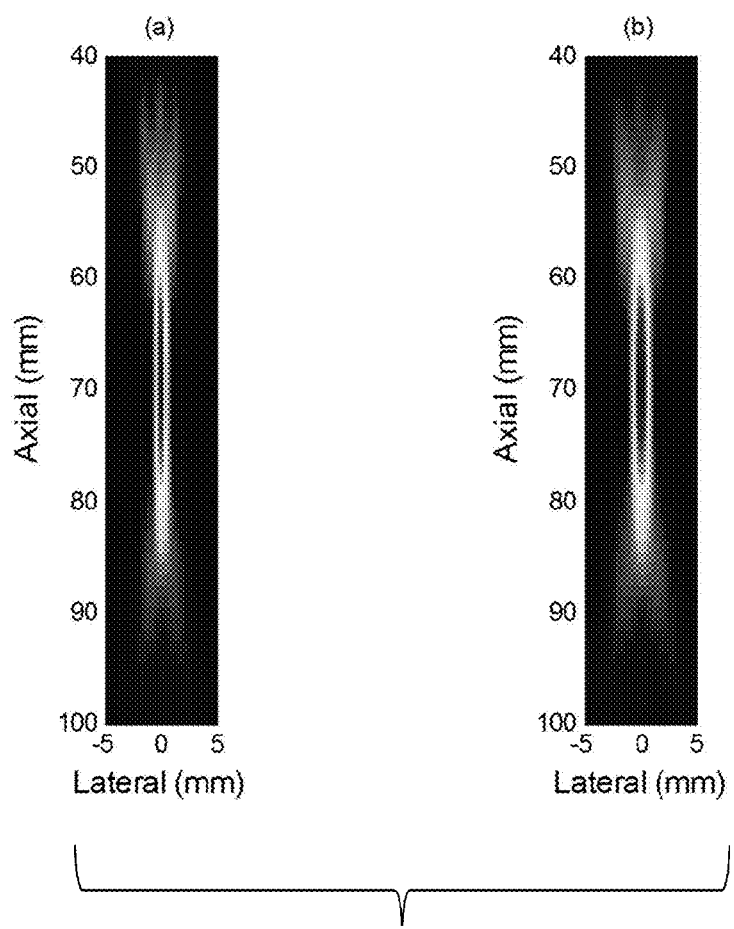
FIG. 2 shows example two-way beam patterns at different center frequencies and apertures for an attenuation of 0.00 dB/cm-MHz.
Figure 3:
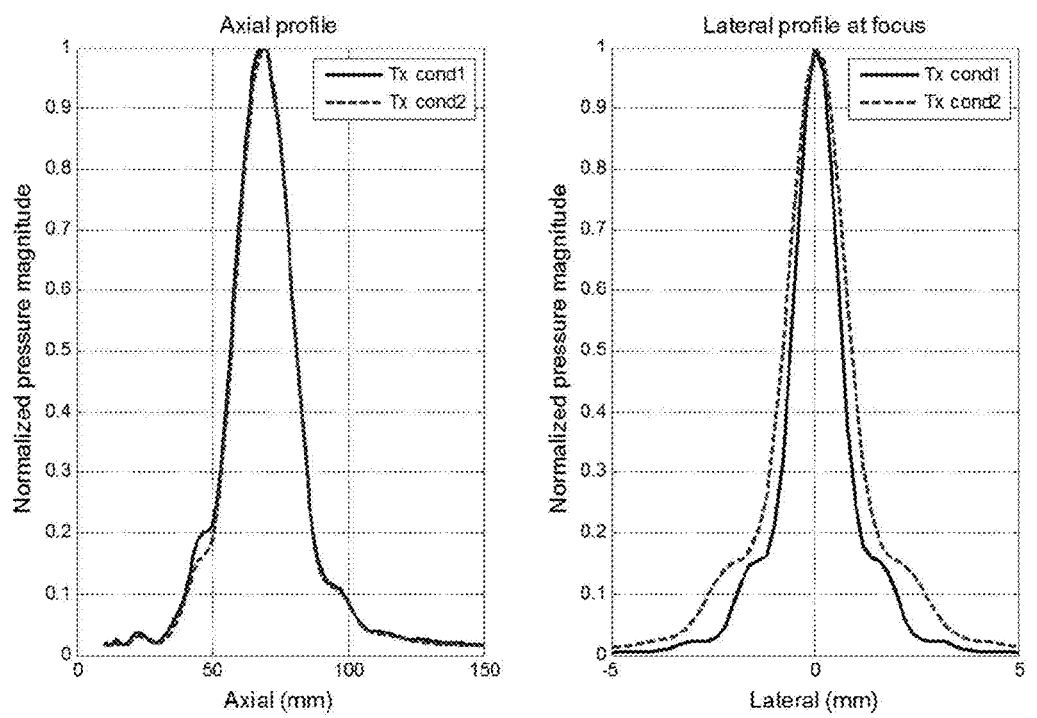
FIG. 3 shows axial and lateral beam profiles corresponding to the beam patterns of FIG. 2.

FIGS. 2-13 show example estimation of attenuation using numerical simulations and phantoms. For FIGS. 2 and 3, the actual attenuation is 0.00 dB/cm-MHz, such as scanning in water. FIG. 2 shows two-way beam patterns. The left side is the two-wave beam pattern for a center frequency of 4 MHz with an F # of 3.0, and the right side is the two-way beam patter for a center frequency of 2 MHz (4/2 MHz) with an F # of the square root of 2 times 3. The frequency is reduced by half, so the aperture is increased by square root of 2, which means the F # increases by square root of two. FIG. 3 shows the axial and lateral profiles corresponding to FIG. 2. The axial profiles match due to the aperture relationship given the frequencies, but the lateral profiles are not matched as the lateral profile relationship is a/lambda as opposed to $a^2$/lambda for the axial profile.

Figure 4:
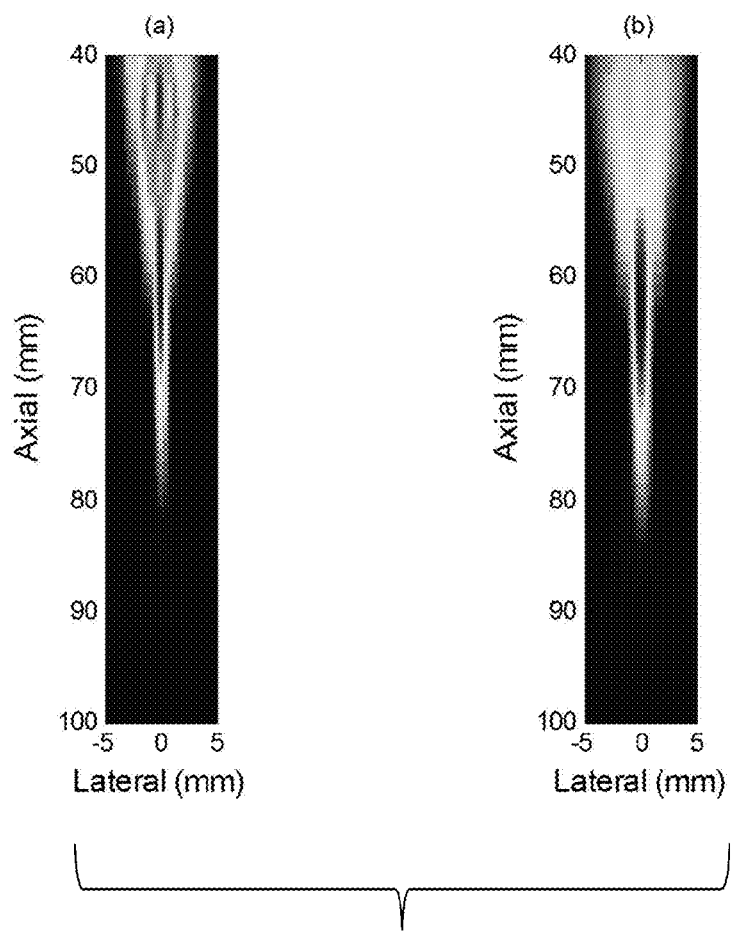
FIG. 4 shows example two-way beam patterns at different center frequencies and apertures for an attenuation of 0.50 dB/cm-MHz.
Figure 5:
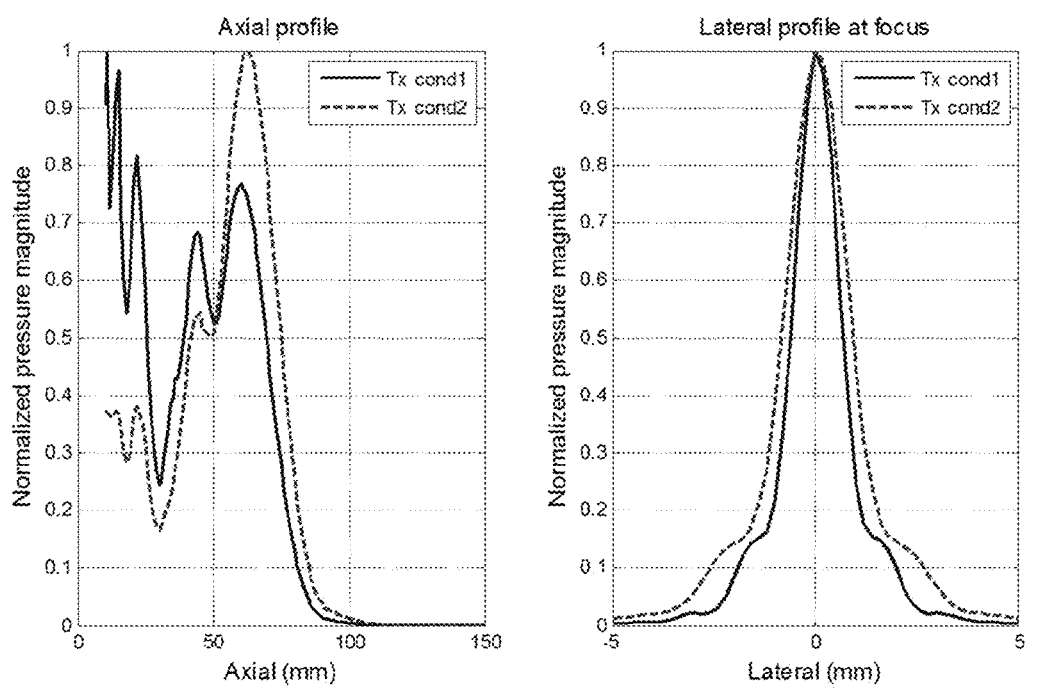
FIG. 5 shows axial and lateral beam profiles corresponding to the beam patterns of FIG. 4.
Figure 6:
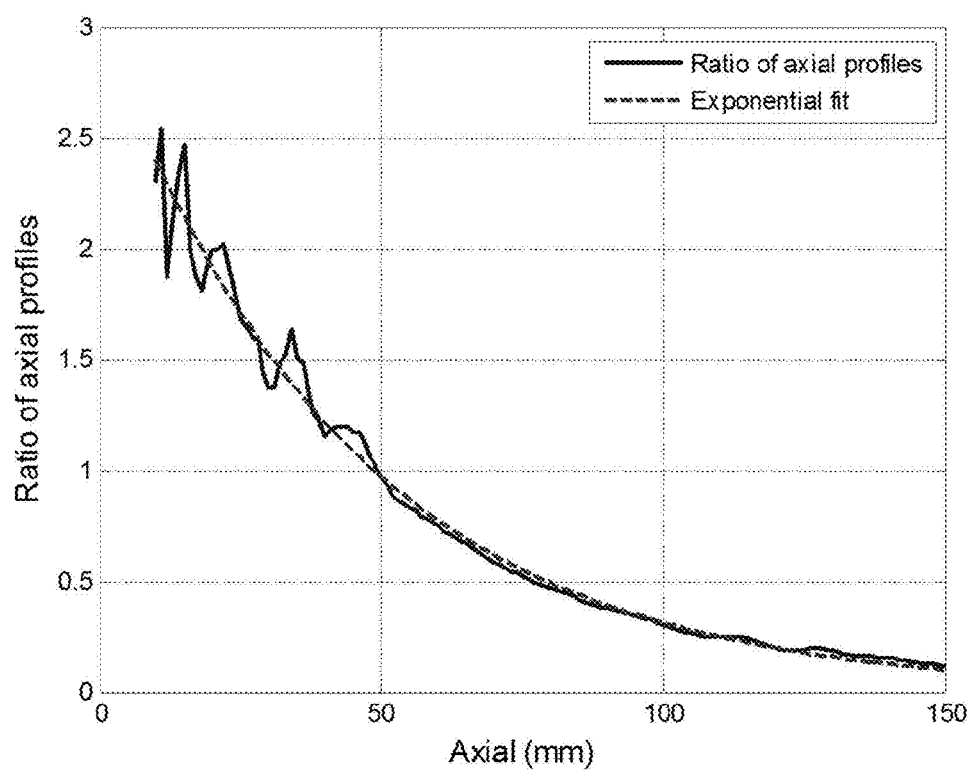
FIG. 6 shows the ratio of the profiles of FIG. 5 and a fit curve to the ratio.

For FIGS. 4-6, the actual attenuation of the numerical phantom is 0.50 dB/cm-MHz. FIG. 4 shows two-way beam patterns. Note that attenuation causes the intensity to fall off more rapidly with depth as compared to FIG. 2. The left side of FIG. 4 is the two-wave beam pattern for a center frequency of 4 MHz with an F # of 3.0, and the right side is the two-way beam patter for a center frequency of 2 MHz (4/2 MHz) with an F # of the square root of 2 times 3.0. FIG. 5 shows the axial and lateral profiles corresponding to FIG. 4. The axial profiles do not match because of attenuation. FIG. 6 shows the ratio of the axial profiles and an exponential fit. The fit yields an attenuation coefficient of 0.49 dB/cm-MHz where the true value is 0.5 dB/cm-MHz.

Figure 7:
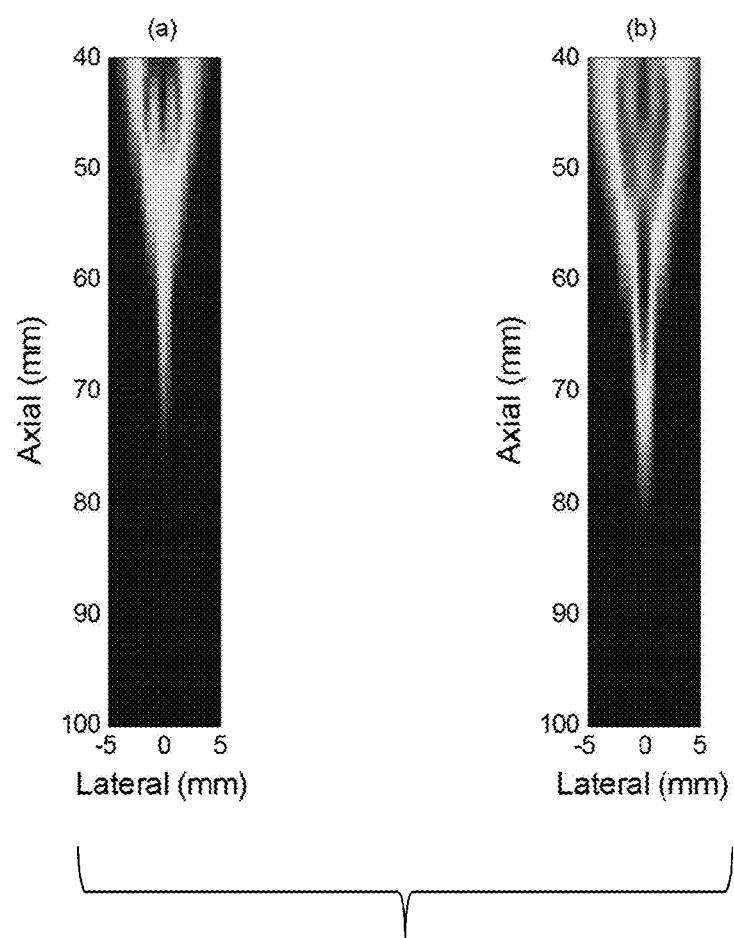
FIG. 7 shows example two-way beam patterns at different center frequencies and apertures for an attenuation of 0.75 dB/cm-MHz.
Figure 8:
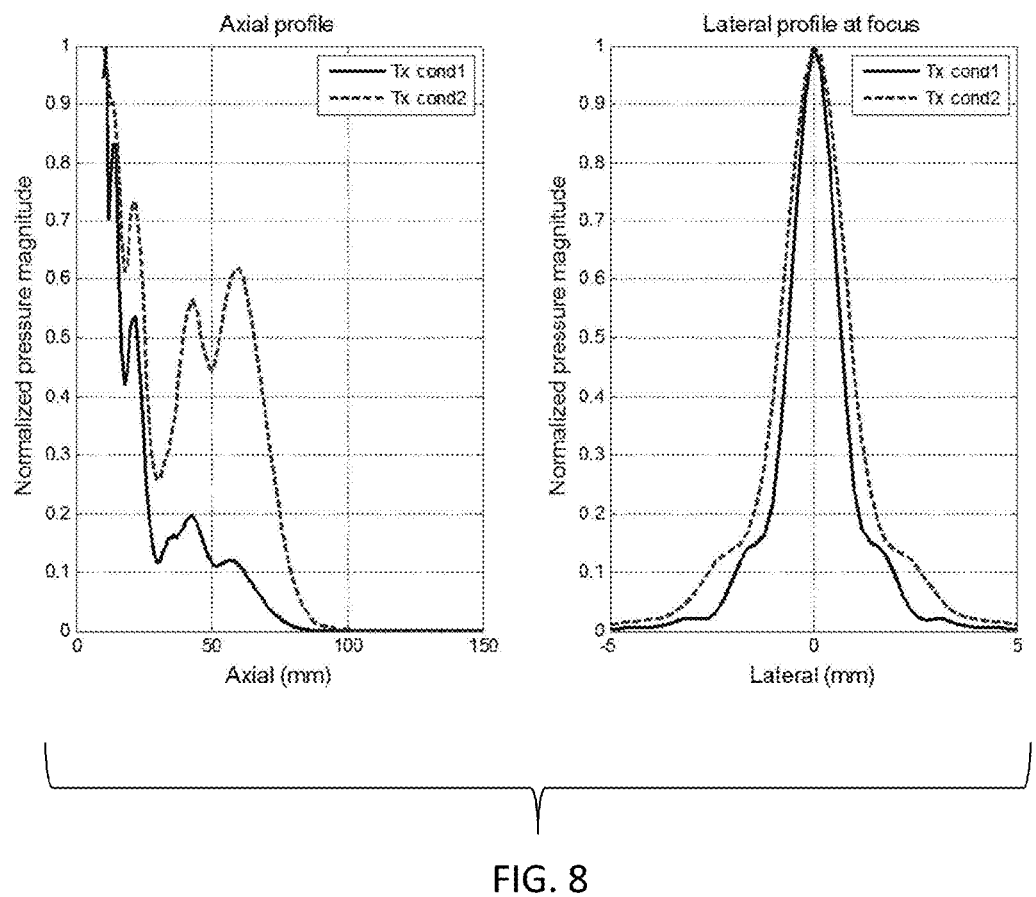
FIG. 8 shows axial and lateral beam profiles corresponding to the beam patterns of FIG. 7.
Figure 9:
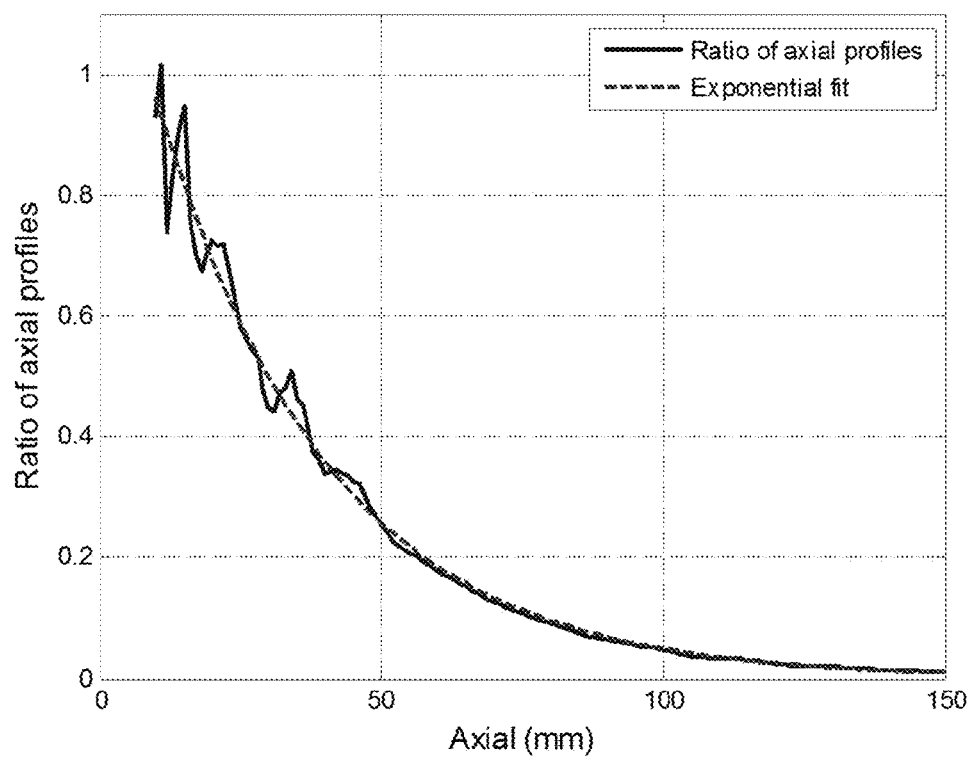
FIG. 9 shows the ratio of the profiles of FIG. 8 and a fit curve to the ratio.

For FIGS. 7-9, the actual attenuation is 0.75 dB/cm-MHz. FIG. 7 shows two-way beam patterns. Note that attenuation causes the intensity to fall off more rapidly with depth as compared to FIGS. 2 and 4. The left side of FIG. 7 is the two-wave beam pattern for a center frequency of 4 MHz with an F # of 3.0, and the right side is the two-way beam patter for a center frequency of 2 MHz (4/2 MHz) with an F # of the square root of 2 times 3.0. FIG. 8 shows the axial and lateral profiles corresponding to FIG. 7. The axial profiles do not match because of attenuation. FIG. 9 shows the ratio of the axial profiles and an exponential fit. The fit yields an attenuation coefficient of 0.714 dB/cm-MHz. The true value is 0.75 dB/cm-MHz.

FIGS. 10-11 and 12-13 show two example measurements of attenuation estimation using ARFI transmissions. Two phantoms are scanned, one with attenuation of 1.5 dB/cm at 3 MHz (~0.5 dB/cm-MHz) (see FIGS. 10-11) and the other with attenuation of 2.4 dB/cm-MHz at 3 MHz (~0.8 dB/cm-MHz) (see FIGS. 12-13). For one ARFI transmission, the push pulse frequency is 2 MHz with a focal depth of 57 mm and an aperture of 25.85 mm. For the other ARFI transmission, the pushing pulse frequency is 4 MHz with a focal depth of 57 mm and an aperture of 17.866 mm.

Figure 10:
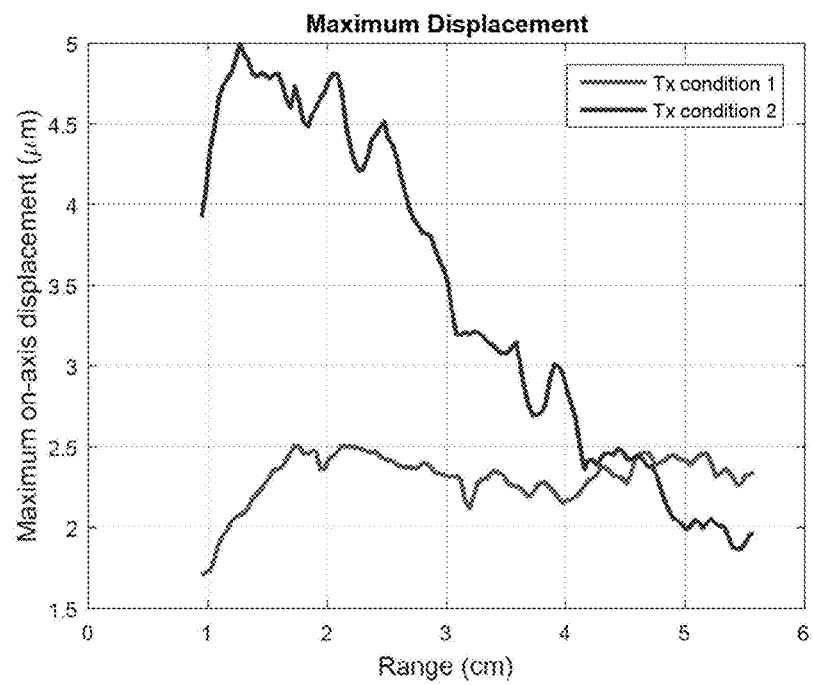
FIG. 10 shows example maximum displacements responsive to pushing pulses at different frequencies and apertures in material with attenuation of 0.50 dB/cm-MHz.
Figure 11:
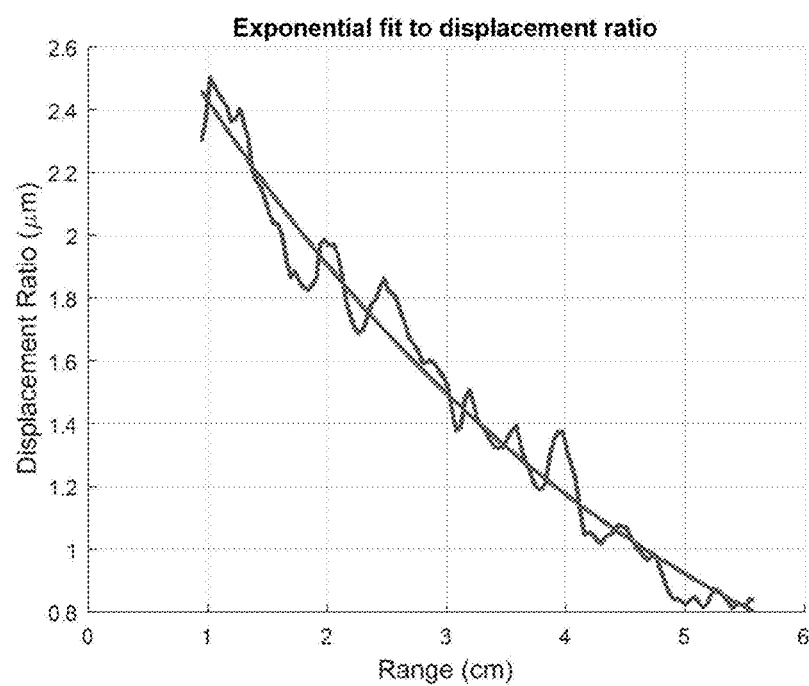
FIG. 11 shows a ratio of the displacement profiles of FIG. 10 and a fit curve to the ratio.
Figure 12:
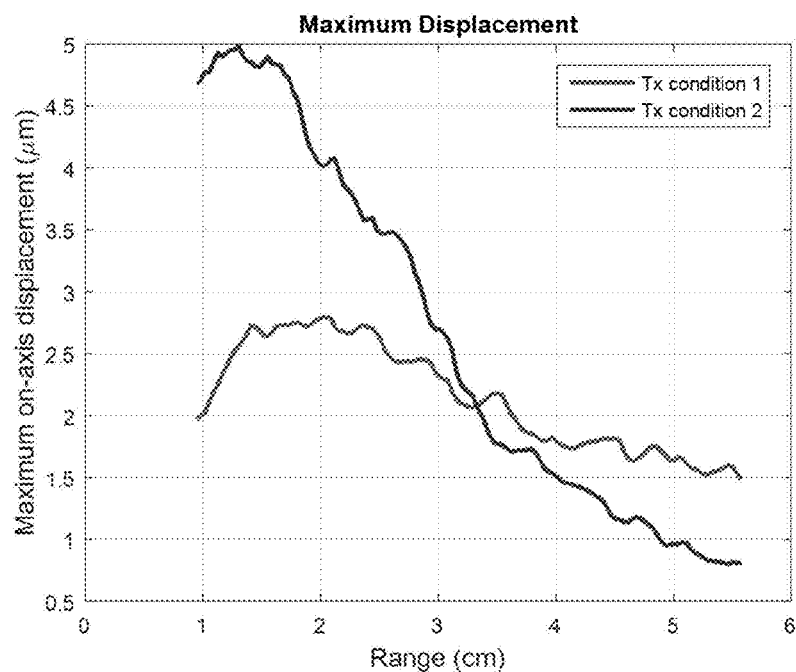
FIG. 12 shows example maximum displacements responsive to pushing pulses at different frequencies and apertures in material with attenuation of 0.75 dB/cm-MHz.
Figure 13:
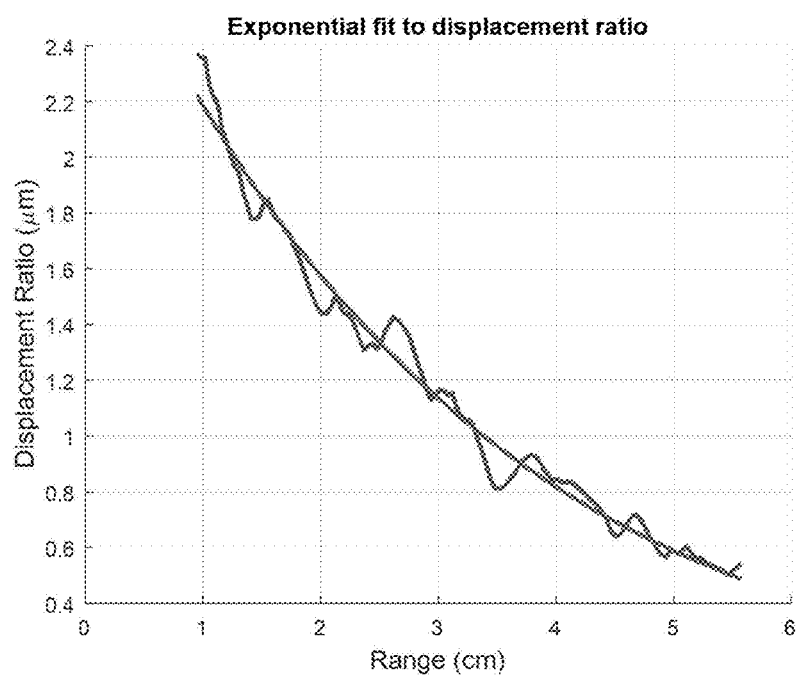
FIG. 13 shows a ratio of the displacement profiles of FIG. 12 and a fit curve to the ratio.

FIGS. 10 and 12 show the displacements as a function of depth responsive to the two ARFI transmissions. FIGS. 11 and 13 show the ratio of displacements over depth and the fit exponential curve. The attenuation for the example of FIGS. 10 and 11 is estimated as 0.53 dB/cm-MHz as compared to the actual 0.5 dB/cm-MHz. The attenuation for the example of FIGS. 12 and 13 is estimated as 0.71 dB/cm-MHz as compared to the actual 0.8 dB/cm-MHz.

FIG. 14 shows one embodiment of a system 10 for estimating attenuation with ultrasound imaging. The medical system 10 measures the attenuation. For example, the medical system 10 implements the method of FIG. 1 or another method. The medical system 10 is an ultrasound scanner using received signals or measures of tissue displacement over depth responsive to transmissions at different frequencies with apertures based on axial profile matching. A ratio of response to the transmissions with different frequencies and respective different aperture sizes is used to estimate the attenuation of tissue.

The medical system 10 includes a transmit beamformer 12, a transducer 14, a receive beamformer 16, an image processor 18, a memory 20, and a display 22. Additional, different or fewer components may be provided. For example, the medical system 10 includes a B-mode or other detector. As another example, the image processor 18, memory 20, and/or display 22 are provided without the front-end components, such as the transmit and receive beamformers 12, 16. In yet another example, a user interface including a user input (e.g., mouse, trackball, keyboard, buttons, knobs, sliders, and/or touch pad) is provided for user indication of a region of interest on an image.

In one embodiment, the medical system 10 is a medical diagnostic ultrasound system. In an alternative embodiment, the system 10 is a computer or workstation.

The transducer 14 is an array of a plurality of elements. The elements are piezoelectric or capacitive membrane elements. The array is configured as a one-dimensional array, a two-dimensional array, a 1.5D array, a 1.25D array, a 1.75D array, an annular array, a multidimensional array, a wobbler array, combinations thereof, or any other now known or later developed array. Planar or curved arrays may be used. The transducer elements transduce between acoustic and electric energies. The transducer 14 connects with the transmit beamformer 12 and the receive beamformer 16 through a transmit/receive switch, but separate connections may be used in other embodiments.

The transmit and receive beamformers 12, 16 are a beamformer for scanning with the transducer 14. The transmit beamformer 12, using the transducer 14, transmits one or more beams into a patient. Vector®, sector, linear or other scan formats may be used. For attenuation estimation, the transmissions may be along a same scan line.

The transmit beamformer 12 is a processor, delay, filter, waveform generator, memory, phase rotator, digital-to-analog converter, amplifier, combinations thereof or any other now known or later developed transmit beamformer components. In one embodiment, the transmit beamformer 12 digitally generates envelope samples. Using filtering, delays, phase rotation, digital-to-analog conversion, and amplification, the desired transmit waveform is generated. Other waveform generators may be used, such as switching pulsers or waveform memories.

The transmit beamformer 12 is configured as a plurality of channels for generating electrical signals of a transmit waveform for each element of a transmit aperture on the transducer 14. The waveforms are unipolar, bipolar, stepped, sinusoidal, or other waveforms of a desired center frequency or frequency band with one, multiple, or fractional number of cycles. The waveforms have relative delay and/or phasing and amplitude for focusing the acoustic energy. The transmit beamformer 12 includes a controller for altering an aperture (e.g. the number of active elements), an apodization profile (e.g., type or center of mass) across the plurality of channels, a delay profile across the plurality of channels, a phase profile across the plurality of channels, center frequency, frequency band, waveform shape, number of cycles, and/or combinations thereof. A transmit beam origin, orientation, and focus are generated based on these beamforming parameters.

The transmit beamformer 12 is configured to generate pulses at different frequency bands using different apertures, respectively. Two or more transmit beams are generated along a same scan line, but with different frequencies and apertures. The transmissions are simultaneous or sequential. The apertures for each transmission are set based on the frequency. The relationship between frequencies of the transmit beams is used to set a relationship between the apertures. The sizes of the apertures are a function of the frequencies of the transmissions.

The transmit beamformer 12 may be configured to generate imaging pulses or pulses for generating echoes. Alternatively or additionally, the transmit beamformer 12 may be configured to generate pushing pulses (ARFI). The transmit beamformer 12 generates a transmit beam for ARFI and transmit beams for measuring resulting displacements. The transmit beam for ARFI is formed at different energy or amplitude levels than the transmit beams for measuring displacements. Amplifiers for each channel and/or aperture size control the amplitude of the transmitted beam. Transmit beams to displace tissue may have greater amplitudes than for imaging or measuring tissue displacement. Alternatively or additionally, the number of cycles in the pulse or waveform used to generate ARFI is greater than for tracking (e.g., 100 or more cycles for ARFI and 1-6 cycles for tracking).

The receive beamformer 16 is a preamplifier, filter, phase rotator, delay, summer, base band filter, processor, buffers, memory, combinations thereof or other now known or later developed receive beamformer components. The receive beamformer 16 is configured into a plurality of channels for receiving electrical signals representing echoes or acoustic energy impinging on the transducer 14. A channel from each of the elements of the receive aperture within the transducer 14 connects to an amplifier and/or delay. An analog-to-digital converter digitizes the amplified echo signal. The digital radio frequency received data is demodulated to a base band frequency. Any receive delays, such as dynamic receive delays and/or phase rotations, are then applied by the amplifier and/or delay. A digital or analog summer combines data from different channels of the receive aperture to form one or a plurality of receive beams. The summer is a single summer or cascaded summer. In one embodiment, the beamform summer is configured to sum in-phase and quadrature channel data in a complex manner such that phase information is maintained for the formed beam. In alternative embodiments, the receive beamformer sums radio frequency data. Other receive beamformers may be used.

The receive beamformer 16 is configured to form receive beams in response to the transmit beams. For example, the receive beamformer 16 receives one, two, or more receive beams in response to each transmit beam for measuring. The phase rotators, delays, and/or summers may be repeated for parallel receive beamformation. The receive beams are collinear, parallel and offset or nonparallel with the corresponding transmit beams.

The receive beamformer 16 is configured to output samples for a single location or multiple locations in a patient. The receive beamformer 16 outputs samples representing locations on-axis with the ARFI beam or with the imaging transmit beams. Dynamic receive operation may be used to generate beamformed samples along the scan line 11. The samples are on-axis, such as at multiple depths along the scan line. The samples are from echoes of transmit beams transmitted for measuring tissue displacement or are from echoes from imaging transmit beams.

Once the channel data is beamformed or otherwise combined to represent locations along the scan line 11, the data is converted from the channel domain to the image data domain. Beamformed samples are output. The samples are responsive to the transmit pulses, so samples are output responsive to transmissions with different frequency bands and respective apertures. The receive beamformer 16 may apply filtering and apertures to match the transmit beams, resulting in one set of samples responsive to a transmit beam and another set of samples responsive to a different transmit beam.

In other embodiments, the received samples are used to track tissue displacement. The receive beamformer 16 or the image processor 18 determines the tissue displacement at a given time after ARFI or over time. The maximum displacement over time may be found.

The image processor 18 is a digital signal processor, a general processor, an application specific integrated circuit (ASIC), field programmable gate array (FPGA), control processor, digital circuitry, analog circuitry, graphics processing unit, combinations thereof, or other now known or later developed device for estimating attenuation. The image processor 18 is configured by hardware, firmware, and/or software, such as operating pursuant to instructions provided in the memory 20 or a different memory. In one embodiment, the image processor 18 is a digital signal processor, ASIC, Doppler detector, or FPGA specifically for performing correlation or other displacement calculation, and another device (e.g., calculator or processor) for estimating the attenuation. In other embodiments, the image processor 18 is a programmable device that performs both the displacement calculation and estimation. Alternatively, the image processor 18 is configured to estimate the attenuation from received signals output by the receive beamformer 16.

The image processor 18 is configured to estimate attenuation at the focal region or along a scan line 11. This estimation is based the samples output from the receive beamformer 16. For example, a ratio of magnitudes of the samples as a function of depth is calculated. Alternatively, the image processor 18 determines the ratio from tissue displacements. The ratio is between the samples responsive to the different transmit beams. The attenuation is estimated as a function of a rate of change fit to the ratio over depth.

The samples or other ultrasound data may be used to generate an image. A B-mode detector, flow estimator (e.g., Doppler processor), or other detector may be provided for detecting characteristics from the receive beamformed samples. A B-mode detector detects the intensity or power of the acoustic backscatter. A flow estimator detects the velocity, energy, or variance of moving objects (e.g., tissue or fluid). The detection may be used to generate an image from which a region of interest for attenuation or other tissue characteristic measurement is selected or on which the estimated attenuation or other tissue characteristic is displayed.

The detector, estimator, and/or the image processor 18 are configured to generate an image. The image includes the tissue characteristic. For example, a graph of the attenuation by location is generated as an image. As another example, alphanumeric text is generated as an image, such as "attenuation=0.71 dB/cm-MHz." In other embodiments, the attenuation value is provided as an annotation on an image of the patient, such as on a B-mode image. In yet other embodiments, one or more pixels corresponding to locations at which the attenuation is estimated are modulated, such as with color, to show the value or values of the attenuation.

The memory 20 is video random access memory, random access memory, removable media (e.g. diskette or compact disc), hard drive, database, or other memory device for storing data. The memory 20 is used by the image processor 18 for storing samples, displacements, relative measurement (e.g., ratio and/or log of the ratio), a fit line, a fit curve, a rate of change, and/or an estimated attenuation.

The instructions for implementing the processes, methods and/or techniques discussed above are provided on computer-readable storage media or memories, such as a cache, buffer, RAM, removable media, hard drive or other computer readable storage media. The memory 20 or a different memory stores the instructions. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display 22 is a CRT, LCD, plasma, projector, monitor, printer, touch screen, or other now known or later developed display device. The display 22 receives RGB, other color values, or other values and outputs an image. The image may be a gray scale or color image. The image displays information that is a function of the attenuation. Alphanumeric, graphical, annotation, or other representation of the attenuation is displayed in an image on the display 22. The image may or may not additionally represent anatomy of the region of the patient scanned by the beamformer 12, 16 and transducer 14.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for characterizing tissue with a medical diagnostic ultrasound scanner, the method comprising:
    transmitting first acoustic energy at a first center frequency with a first aperture of a transducer array;
    transmitting second acoustic energy at a second center frequency with a second aperture of the transducer array, the second center frequency being different than the first center frequency, and the second aperture being different than the first aperture to compensate for frequency dependent diffraction over depth as if no attenuation occurs;
    receiving, by a receive beamformer connected with the transducer array, first and second signals responsive to the first and second acoustic energy, respectively, the first and second signals responsive to tissue of a patient over depth;
    calculating, by an image processor, a ratio of magnitudes of the first signals to the second signals as a function of the depth;
    fitting, by the image processor, a rate of change as a line or curve over depth to the ratio as the function of the depth, the fitting solving for a term of an equation defining the line or curve with respect to depth, the equation having an exponential term relating depth and ratio of the first and second frequencies;
    estimating, by the image processor, attenuation of the tissue in a region of interest having multiple depths from the rate of change over the depth, the term of the equation solved by the fitting providing the attenuation; and
    displaying the attenuation for the patient.

2. The method of claim 1 wherein transmitting the first and second acoustic energies occurs sequentially.

3. The method of claim 1 wherein transmitting the first and second acoustic energies occurs, at least in part, simultaneously.

4. The method of claim 1 wherein transmitting the first and second acoustic energies comprises transmitting with pulses of five or more cycles, and wherein calculating the ratio comprises calculating the ratio with the magnitudes being squares of absolute values of the first and second signals.

5. The method of claim 1 wherein transmitting the first and second acoustic energies comprises transmitting with pulses of four or fewer cycles, and wherein calculating the ratio comprises Fourier transforming the first and second signals, selecting transformed information at the first and second center frequencies, and calculating the ratio from the selected information.

6. The method of claim 1 wherein transmitting the first and second acoustic energies comprises transmitting with the second center frequency twice the first center frequency and the second aperture being smaller than the first aperture by a factor of about 1.4.

7. The method of claim 1 wherein transmitting the first and second acoustic energies comprises transmitting with the first and second apertures being a function of the first and second center frequencies, respectively.

8. The method of claim 7 wherein the second center frequency is smaller than the first center frequency by a factor, and wherein the second aperture is larger than the first aperture by a square root of the factor.

9. The method of claim 1 wherein transmitting the first and second acoustic energies comprises transmitting with the first and second apertures having relative sizes set to match on-axis beam profiles of the first and second acoustic energies.

10. The method of claim 1 wherein receiving comprises receiving the first signals at the first center frequency with a third aperture and receiving the second signals at the second center frequency with a fourth aperture, the fourth aperture being a ratio of the first and second frequencies of the third aperture, and a first bandwidth being used for receiving both the first and second signals.

11. The method of claim 1 wherein fitting comprises fitting the line to a natural logarithm of the ratio as the function of the depth.

12. The method of claim 1 wherein fitting comprises fitting the exponential term to the ratio as the function of the depth.

13. The method of claim 1 wherein displaying the attenuation comprises displaying an alphanumeric representation of the attenuation.

14. The method of claim 1 wherein displaying the attenuation comprises displaying an image of a spatial distribution of the attenuation.

15. A system for estimating attenuation with ultrasound imaging, the system comprising:
- a transmit beamformer configured to generate pulses at different frequency bands using different apertures, respectively, the transmit beamformer configured to form the apertures to have sizes of the apertures set with a function of the frequency bands where, for each of the apertures, the function for the size is a square of the size of the aperture divided by a wavelength for a center frequency of the frequency band, the function being a correction for diffraction effects as if there is no attenuation so that on-axis intensity profiles of the pulses match;
- a receive beamformer configured to output samples responsive to the pulses;
- an image processor configured to estimate attenuation from a distortion in the match caused by the attenuation from the samples; and
- a display configured to display the attenuation.

16. The system of claim 15 wherein the receive beamformer comprises a dynamic beamformer capable of varying apertures over depth and is configured to form first and second receive apertures on a transducer, the first and second receive apertures as formed by the dynamic beamformer being relatively sized to each other by a ratio of the first and second frequency bands, configured to receive first and second signals responsive to the pulses at the first and second frequency bands with the first and second receive apertures, respectively, and configured to output the samples from the first and second signals where the samples are at the first and second frequency bands, and wherein the image processor is configured to estimate the attenuation as a function of a rate of change, the rate of change being a fit to a ratio of magnitudes of the samples.

17. A method for estimation tissue attenuation with a medical diagnostic ultrasound scanner, the method comprising:
- transmitting first acoustic energy at a first center frequency with a first aperture of a transducer array;
- transmitting second acoustic energy at a second center frequency with a second aperture of the transducer array, the second center frequency being different than the first center frequency by a factor, and the second aperture being set to be different in size than the first aperture using an inverse of the square root of the factor to set the size, the factor being a correction for diffraction effects as if there is no attenuation so that on-axis intensity profiles of the transmitted first and second acoustic energies match;
- receiving, by a receive beamformer connected with the transducer array, first and second signals responsive echoes of the first and second acoustic energy, respectively, from tissue;
- estimating, by an image processor, the tissue attenuation from a distortion in the match caused by the attenuation reflected in a ratio responsive to the first and second signals; and
- generating an image of the attenuation for the patient.

18. The method of claim 17 wherein estimating comprises estimating from a rate of change in the ratio as a function of depth, the ratio being of magnitudes of the first and second signals at the first and second center frequencies.

* * * * *